(12) United States Patent
Reinboth (10) Patent No.: US 10,709,823 B2
(45) Date of Patent: Jul. 14, 2020

(54) SYSTEM AND DEVICE FOR COLLECTING LIQUIDS

(71) Applicant: Drägerwerk AG & Co. KGaA, Lübeck (DE)

(72) Inventor: Thomas Reinboth, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 289 days.

(21) Appl. No.: 15/679,653

(22) Filed: Aug. 17, 2017

(65) Prior Publication Data

US 2018/0050135 A1 Feb. 22, 2018

(30) Foreign Application Priority Data

Aug. 18, 2016 (DE) .................. 10 2016 009 918

(51) Int. Cl.
*A61M 1/00* (2006.01)

(52) U.S. Cl.
CPC ........ *A61M 1/0001* (2013.01); *A61M 1/0007* (2014.02); *A61M 1/005* (2014.02); *A61M 1/0013* (2013.01); *A61M 1/0052* (2014.02); *A61M 1/0096* (2014.02); *A61M 2205/128* (2013.01)

(58) Field of Classification Search
CPC .......... A61M 1/0001; A61M 2205/128; A61M 1/005; A61M 1/0007; A61M 1/0096; A61M 1/0052; A61M 1/0023; A61M 1/0013

See application file for complete search history.

(56) References Cited

U.S. PATENT DOCUMENTS

| | | | | |
|---|---|---|---|---|
| 5,391,351 | A * | 2/1995 | Kaufman | A61L 11/00 206/219 |
| 5,624,417 | A * | 4/1997 | Cook | A61M 1/0001 604/319 |
| 6,056,731 | A | 5/2000 | Koetke et al. | |
| 2007/0170104 | A1* | 7/2007 | Belford | B01D 29/117 210/295 |
| 2009/0012493 | A1* | 1/2009 | Harig | A61M 1/0003 604/404 |

(Continued)

FOREIGN PATENT DOCUMENTS

| | | |
|---|---|---|
| CN | 202620317 U | 12/2012 |
| DE | 197 23 197 A1 | 12/1998 |
| DE | 4142089 C2 | 5/2000 |

(Continued)

*Primary Examiner* — Peter S Vasat
*Assistant Examiner* — Meagan Ngo
(74) *Attorney, Agent, or Firm* — McGlew and Tuttle, P.C.

(57) ABSTRACT

A system (1) for collecting liquid, including a main collecting chamber (10), a main duct section (11, 12, 13) connected to the main collecting chamber (10) in a fluid-communicating manner, and an auxiliary collecting chamber (20, 30, 40). The system (1) has an auxiliary duct section (21, 38, 39) connected to the auxiliary collecting chamber (20, 30, 40) in a fluid-communicating manner for connection to the main duct section (11, 12, 13). The main duct section (11, 12, 13) and the auxiliary duct section (21, 38, 39) form a duct (35, 36, 37) when the main duct section is connected to the auxiliary duct section. A water-soluble closing component (14, 15, 16) closes the duct (35, 36, 37). A hygienic collecting device for liquid, which has a short evacuation time and a flexible collection volume, is provided with the system (1).

19 Claims, 3 Drawing Sheets

(56) References Cited

U.S. PATENT DOCUMENTS

2013/0310811 A1* 11/2013 Green ............... A61M 25/0017
604/544
2014/0291218 A1   10/2014 Bluchel et al.

FOREIGN PATENT DOCUMENTS

| EP | 2011528 A2 | 1/2009 |
| WO | 96/05873 A1 | 2/1996 |
| WO | 2016/116314 A1 | 7/2016 |

* cited by examiner

SYSTEM AND DEVICE FOR COLLECTING LIQUIDS

CROSS REFERENCE TO RELATED APPLICATIONS

This application claims the benefit of priority under 35 U.S.C. § 119 of German Application 10 2016 009 918.6 filed Aug. 18, 2016, the entire contents of which are incorporated herein by reference.

FIELD OF THE INVENTION

The present invention pertains to a system for collecting liquids, comprising a main collecting chamber, a main duct section connected to the main collecting chamber in a fluid-communicating manner and an auxiliary collecting chamber.

BACKGROUND OF THE INVENTION

A suction device is specified for surgeries or other medical treatments in order to make it possible to clear the throat by suction in case the patient vomits. Further, body fluids, which obstruct the view to the wound, are suctioned and collected in collecting containers. The collecting containers are disposed of after the surgery. The collecting containers must collect body fluids hygienically, i.e., the body fluids must not escape to the outside and also not into the pumping device.

It is known that full collecting containers may be replaced with empty collecting containers during the surgery. However, the suction of the body fluid is interrupted hereby. Even if collecting containers of different sizes are available, the quantity of body fluid that will be discharged and must then be collected must be estimated in advance. Should this estimate be incorrect, it will be necessary to change the collecting container despite the preparatory estimation. The surgeon cannot optimally see the wound any longer due to the interruption during the replacement of the collecting container and the time needed for the entire surgery may become longer, which is disadvantageous for the patient. If an excessively large collecting container was selected, the work process is inefficient, because a collecting container is not usually used for a plurality of surgeries for hygienic reasons.

Further, the time needed for evacuating the container, during which no wound secretion can be suctioned, will increase.

It is known in this connection that a plurality of collecting containers may be connected in series or parallel. The containers are equipped here with valves, which are opened via floats, which indicate the filling level in the collecting container being filled. This device, with the combination of the floats and valves, has a complicated configuration and is susceptible to malfunction, because, for example, a float may be stuck or an error may occur in the valve control and the corresponding valve will not consequently open or will not open in time.

SUMMARY OF THE INVENTION

An object of the present invention is to provide an alternative hygienic collecting device for liquid, which makes possible a short evacuation time and flexible collection volume.

In a system for collecting liquids, comprising a main collecting chamber, a main duct section connected to the main collecting chamber in a fluid-communicating manner and an auxiliary collecting chamber, provisions are made according to the present invention for the system to have an auxiliary duct section connected to the auxiliary collecting chamber in a fluid-communicating manner for connection to the main duct section, wherein the main duct section and the auxiliary duct section form a duct when the main duct section is connected to the auxiliary duct section, wherein a water-soluble closing component closes the duct.

Thus, the system comprises a main collecting chamber, which may be complemented by an additional auxiliary collecting chamber. Only the main duct section and the auxiliary duct section are connected to one another for this. These then form a duct that connects the main collecting chamber and the auxiliary connection chamber to one another. Based on the fluid-communicating connection, liquid can flow from the main collecting chamber into the auxiliary collecting chamber. The volume of the auxiliary collecting chamber is thus added to the volume of the main collecting chamber. Further, automatic opening of the duct is brought about by means of the water-soluble closing component when liquid reaches the water-soluble closing component. The water-soluble closing component dissolves on contact with liquid and releases the duct. Automatic opening of the duct is thus brought about without valves having to be actuated. The contact of the water-soluble closing component with liquid brings about the opening of the duct directly. The volume of the auxiliary collecting chamber is therefore used only when it is also actually needed. A flexible collection volume is thus provided. Further, there is no interruption in the suction process during the addition of the additional volume of the auxiliary collecting chamber to the volume of the main collecting chamber. Since the volume of the auxiliary collecting chamber is relatively small compared to the overall volume, only a small volume must be evacuated after opening the duct before liquid can flow into the auxiliary collecting chamber. The switchover thus takes place rapidly, simply and hygienically. Further, the system is more cost-effective than previous systems, because it can be manufactured in a simple manner and only a size variant of the system must be provided.

The water-soluble closing component may be configured as a water-soluble film and inserted into the duct or placed at a discharge or inlet opening to the duct for closing the duct such that no liquids and hence also no solid particles can pass through the duct, except after the dissolution of the water-soluble closing component due to contact with water or a liquid containing water. It is, of course, preferably also possible to use as the water-soluble closing component a material, preferably in the form of a film, which is impermeable to both liquids not containing water and to gases.

In particular, the water-soluble closing component may be a film consisting of polyvinyl alcohol (PVAL).

The water-soluble closing component may be fastened to or in the duct, for example, by bonding.

The water-soluble closing component is advantageously arranged at the main duct section. This means that the water-soluble closing component closes the main duct section as long as no water-containing liquid reaches it. Likewise, the duct remains closed by the water-soluble closing component even if the auxiliary duct section is connected to the main duct section. This has the advantage that the auxiliary collecting chamber may have a simple configuration and may be manufactured from only a few components in a cost-effective manner.

The water-soluble closing component is advantageously arranged at the auxiliary duct section, the auxiliary collecting chamber preferably being evacuated. The water-soluble closing component thus closes the auxiliary duct section and, as a result, also the auxiliary collecting chamber. When the main duct section is connected to the auxiliary duct section, the duct likewise remains closed by the water-soluble closing component as long as no liquid comes into contact with the water-soluble closing component. Further, the closure of the auxiliary collecting chamber makes it possible to evacuate the auxiliary collecting chamber before the closure. The water-soluble closing component is configured here such that it can withstand the pressure difference between the ambient pressure and the evacuation pressure without being damaged. The pre-evacuation has the advantage that the volume of the auxiliary collecting chamber does not need to be evacuated when the duct is opened. The suction process can thus be continued smoothly, without there being a brief interruption due to an evacuation of the auxiliary collecting chamber. Another water-soluble closing component at the main duct section is not necessary, but it may, of course, be used additionally.

The main collecting chamber preferably has a suction pump port and a liquid inlet opening, which are connected to the main collecting chamber in a fluid-communicating manner.

It is further advantageous if the main duct section has a blocking component, which closes the main duct section when the main duct section and the auxiliary duct section are separated from one another, and which is opened when the main duct section and the auxiliary duct section are connected to one another.

It is thus ensured that the main duct section is opened only when the main duct section is connected to the auxiliary duct section. Even if liquid enters the main duct section and a possibly present water-soluble closing component opens in this manner, no liquid can escape through the main duct section to the outside as long as there is no connection between the main duct section and an auxiliary duct section. The main collecting chamber can thus still be filled with liquid when the liquid level has risen to the extent that it has reached the main duct section. Without the blocking component, the main collecting chamber could be filled with liquid only as long as the liquid level reaches the main duct section, and the liquid must not yet enter the main duct section.

The blocking component may be arranged in the main duct section in the form of, for example, a diaphragm. The diaphragm is made of a material that is not soluble in water and is impermeable to liquids as well as preferably also to gases. For example, the diaphragm may consist of PTFE (polytetrafluoroethylene), natural rubber or silicone rubbers. The latter may also be coated with PTFE. Such diaphragms are also used, for example, as puncturable rubber in perforable vials or in infusion bags.

A blocking component configured as such a diaphragm is opened when the connection is established between the main duct section and the auxiliary duct section by being punctured by the auxiliary duct section, which is beveled, for example, in the shape of a mandrel or is configured as a cannula. Even though the diaphragm is damaged by this manner of opening, the structure and the elasticity of the diaphragm may preferably be such that areas of the diaphragm pushed aside during the puncturing with the auxiliary duct section not only enclose the auxiliary duct section in a sealing manner but also assume their original position again after removal of the auxiliary duct section. The discharge of liquid from the main duct section can be prevented or even stopped even after removal of the auxiliary duct section.

Embodiment variants of a blocking component that make possible a reversible opening and closing of the blocking component are, of course, also possible. For example, a blocking component could also be configured as a flap opening in the direction of the main duct section, which flap is enclosed by a sealing lip in the closed state. In particular, such a flap may have a resetting mechanism, for example, a spring, by which the flap is closed again after removal of the auxiliary duct section in order to prevent the discharge of liquid.

A sealing element, not shown, may be arranged at the main duct section and/or at the auxiliary duct section such that a connection point between the main duct section and the auxiliary duct section is sealed against the surrounding area. Liquid can be prevented in this manner from reaching the surrounding area after opening the blocking component.

A gel is advantageously arranged in the main collecting chamber and preferably in the auxiliary collecting chamber. The gel absorbs the collected liquid and thus increases the viscosity of the liquid. Large quantities of liquid cannot thus slosh around in the collecting chamber, which improves the ease of handling of the system. Furthermore, liquid can thus be prevented from being discharged in the upper areas of the system due to possible leaks, for example, during transportation or during disposal.

The main collecting chamber may advantageously have at least two main duct sections, and the system has at least two auxiliary collecting chambers and at least two auxiliary duct sections connected to an auxiliary collecting chamber each in a fluid-communicating manner for connection to one of the main duct sections each, the main duct sections and the auxiliary duct sections forming a duct each when they are connected to one another, and the duct is closed by a respective water-soluble closing component.

Additional auxiliary collecting chambers may thus be attached to the main collecting chamber. The volume of the main collecting chamber can thus be expanded in a flexible manner. The flexibility of the system is thus increased.

It is further advantageous if the main duct sections comprise an overflow edge component each, the overflow edge components being arranged between the main collecting chamber and the respective main duct section and having a different distance each from a bottom component of the main collecting chamber.

A predefined filling level, beginning from which the main duct section can be wetted with liquid, can be set with the overflow edge component. Liquid enters the main duct section only when the filling level of the main collecting chamber is above the level of the overflow edge component. The water-soluble closing component may preferably be arranged at the overflow edge component. The water-soluble closing component is thus wetted with liquid and dissolved immediately after the overflow of the liquid over the overflow edge.

The present invention further pertains to a device for collecting liquid, comprising a main collecting chamber and a main duct section connected to the main collecting chamber in a fluid-communicating manner, in which provisions are made according to the present invention for a water-soluble closing component closing the main duct section, wherein the main collecting chamber is preferably perfected according to the features of the above description.

The present invention further pertains to a device for collecting liquid, comprising an auxiliary collecting chamber and an auxiliary duct section connected to the auxiliary collecting chamber in a fluid-communicating manner, in which provisions are made according to the present invention for a water-soluble closing component closing the auxiliary duct section, wherein the auxiliary collecting chamber is preferably pre-evacuated.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Referring to the drawings, the system for collecting liquid is designated as a whole by the reference number 1. The system 1 comprises here a main container 2 and at least one auxiliary container 3, 4, 5.

Figure 1:
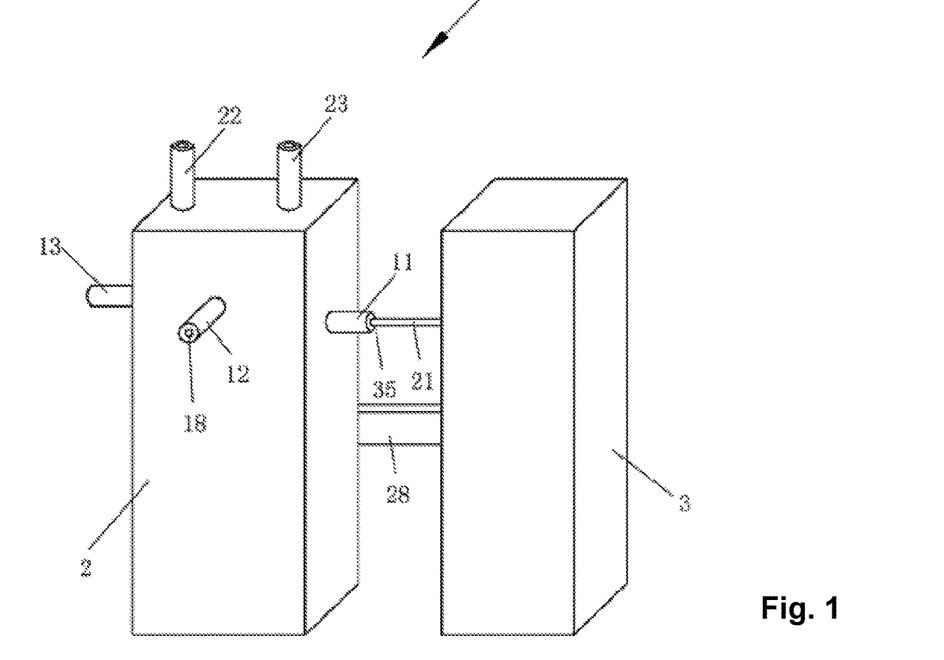
FIG. 1 is a schematic view of the system with an auxiliary collecting chamber.

FIG. 1 shows a main container 2 and a first auxiliary container 3. The main container 2 and the first auxiliary container 3 are connected to one another by means of a first duct 35. Further, the first auxiliary container 3 is fastened to the main container 2 by means of a fastening component 28.

The main container 2 further has a suction pump port 22 and a liquid inlet opening 23. The main container 2 is connected to a suction pump, not shown, via the suction pump port 22. The liquid inlet opening 23 is connected to a wound in a fluid-communicating manner, and liquid of the wound flows through the liquid inlet opening 23 into the main container 2.

Figure 2A:
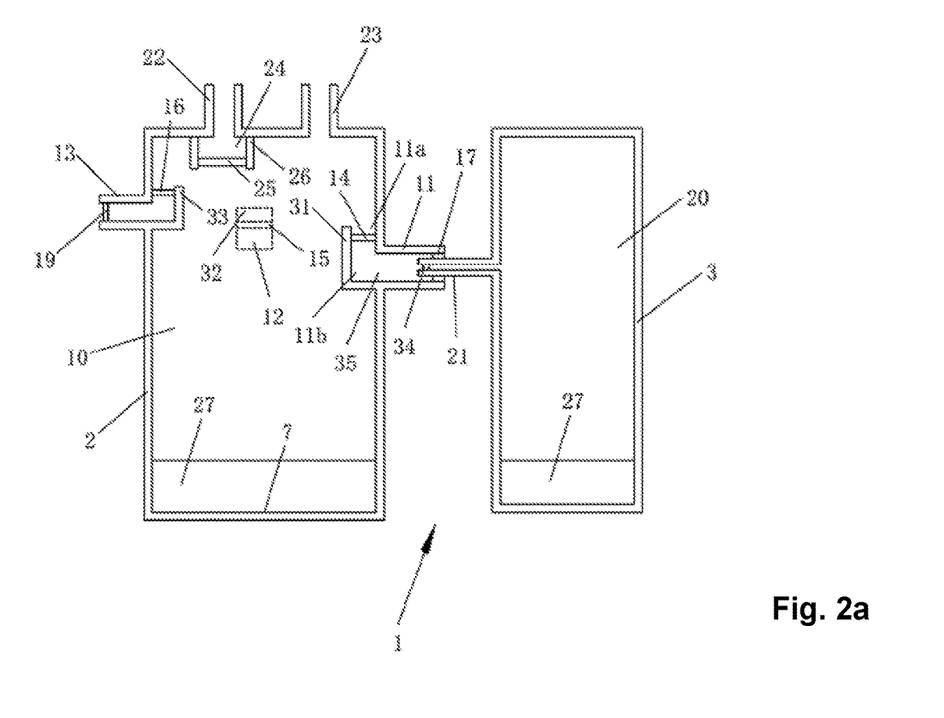
FIG. 2a is a schematic cross-sectional view of the system according to FIG. 1.
Figure 2B:
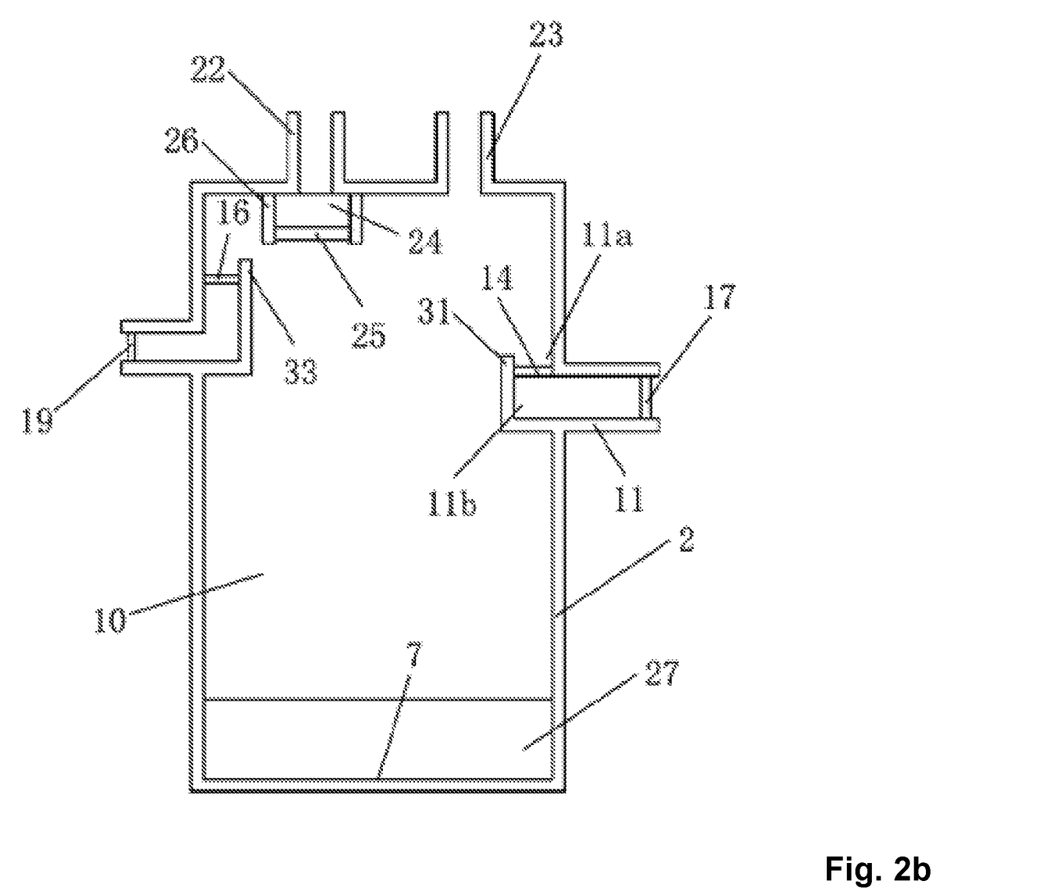
FIG. 2b is a schematic cross-sectional view of a main container of the system according to FIG. 1.

The main container 2 further has a main collecting chamber 10, as is shown in FIG. 2a and FIG. 2b. The suction pump port 22 and the liquid inlet opening 23 are connected to the main collecting chamber 10 in a fluid-communicating manner. The main collecting chamber 10 is evacuated via the suction pump port 22. The vacuum generated thereby in the main collecting chamber 10 is applied up to the wound via the liquid inlet opening 23. This means that suction of liquid can take place at the wound.

Further, a first main duct section 11, a second main duct section 12 and a third main duct section 13, which are connected to the main collecting chamber 10 in a fluid-communicating manner, are arranged at the main container 2. However, a different number of main duct sections 11, 12, 13 may also be present in the system 1. Three main duct sections 11, 12, 13 make it possible for the main container 2 to be configured in a four-sided manner. One main duct section 11, 12, 13 each may now be provided on three sides of the main container 2. The fourth side may be used to fasten the main container 2.

The first main duct section 11 is closed by a first water-soluble closing component 14, the second main duct section 12 by a second water-soluble closing component 15 and the third main duct section 13 by a third water-soluble closing component 16. The water-soluble closing components 14, 15, 16 are configured, as an example, as water-soluble films. A water-soluble film 14, 15, 16 now separates the respective main duct section 11, 12, 13 into two parts. One part of the main duct section 11, 12, 13 remains connected to the main collecting chamber 10 in a fluid-communicating manner. The other part of the main duct section 11, 12, 13 is now separated by the water-soluble film 14, 15, 16 from the main collecting chamber 10 until the water-soluble film 14, 15, 16 is dissolved by the contact with liquid.

This is explained in more detail based on the example of the first main duct section 11. The part of the first main duct section 11 that is in connection with the main collecting chamber 10 in a fluid-communicating manner when the first water-soluble film 14 has not yet dissolved is designated by the reference number 11a. The other part, which is separated by the first water-soluble film 14, is designated by the reference number 11b.

A first auxiliary collecting chamber 20, which is arranged in the first auxiliary container 3, is provided in FIG. 2a. A first auxiliary duct section 21, which is connected to the first auxiliary collecting chamber 20 in a fluid-communicating manner, leads from the first auxiliary collecting chamber 20 into the first main duct section 11. The first auxiliary duct section 21 and the first main duct section 11 now form the first duct 35. The duct 35 connects the main collecting chamber 10 and the auxiliary collecting chamber 20. As soon as the water-soluble film 14 is dissolved, a fluid-communicating connection is formed via the first duct 35 between the main collecting chamber 10 and the first auxiliary collecting chamber 20.

As an alternative or in addition, the first auxiliary duct section 21 may have a fourth water-soluble closing component 34, hereinafter in the form of a water-soluble film as an example, which closes the first auxiliary duct section 21. The first water-soluble film 14 at the main duct section 11 may be eliminated in this case. The first duct 35 connects the main collecting chamber 10 to the first auxiliary collecting chamber 20 in this case in a fluid-communicating manner only when the first water-soluble film 34 at the auxiliary duct section 21 was dissolved.

The fourth water-soluble film 34 at the first auxiliary duct section 21 further enables the first auxiliary collecting chamber 20 to be configured as a pre-evacuated chamber. A vacuum is thus already present in the first auxiliary collecting chamber 20 on connection to the main collecting chamber 10, so that the first auxiliary collecting chamber 20 does not need to be evacuated first after connection to the main collecting chamber 10. Interruption of the suction process due to the connection of the auxiliary collecting chamber 20 is thus avoided.

The first main duct section 11 can additionally be closed by means of a first blocking component 17, the second main duct section 12 can additionally be closed by means of a second blocking component 18, and the third main duct section 13 can additionally be closed by means of a third blocking component 19. As an example, the blocking components 17, 18, 19 are configured as self-closing diaphragms. The respective blocking component 17, 18, 19 is opened as soon as a connection is established between a main duct section 11, 12, 13 and the respective auxiliary duct section 21, 38, 39.

The first blocking component 17 was opened in FIG. 2a by the first auxiliary duct section 21, beveled, for example, in a mandrel-shaped manner or as a cannula, having punctured the blocking component 17, was inserted into the first main duct section 11. Due to the insertion of the first auxiliary duct section 21 into the first main duct section 11, a connection is established between the first main duct section 11 and the first auxiliary duct section 21, so that the first duct 35 is formed.

The second blocking component and the third blocking component 19 are not yet opened and they close the second and third main duct sections 12, 13, respectively. No liquid can thus flow from the main collecting container 10 through the second or third main duct section 12, 13. The main collecting chamber 10 cannot lose any collected liquid in this manner via the second or third main duct section 12, 13.

A sealing component, not shown, may be arranged at the main duct section 11, 12, 13 and/or at the auxiliary duct sections 21, 38, 39 connected thereto such that a connection point between the main duct section 11, 12, 13 and the respective auxiliary duct section 21, 38, 39 is sealed against the surrounding area. Liquid can be prevented in this manner from entering the surrounding area after opening a blocking component 17, 18, 19. The first main duct section 11 comprises a first overflow edge component 31, the second main duct section 12 comprises a second overflow edge component 32, and the third main duct section 13 comprises a third overflow edge component 33. The overflow edge components 31, 32, 33 have different distances compared to one another from a bottom 7 of the main collecting chamber 10. This means that when the liquid level rises, the overflow edge components 31, 32, 33 are at the same level as the liquid surface of the collected liquid in the main collecting container 10 at different times.

According to FIG. 2a, the main duct sections 11, 12, 13 are likewise arranged at different levels in a first preferred embodiment.

In a second preferred embodiment according to FIG. 2b, the main duct sections 11, 12, 13 are arranged at the same level. Only the overflow edge components 31, 32, 33 within the main container 2 have different distances from the bottom 7 of the main collecting chamber 10.

Further, the water-soluble films 14, 15, 16 may be arranged at the overflow edge components 31, 32, 33. According to FIG. 2a, they may be arranged horizontally, so that liquid that flows over the overflow edge component 31, 32, 33 will collect on the corresponding water-soluble film 14, 15, 16. The liquid is now distributed on the surface of the water-soluble film 14, 15, 16, so that the water-soluble film 14, 15, 16 is wetted with liquid on its entire surface pointing upward and is thus completely dissolved. The liquid can then further enter into the main duct section 11, 12, 13 and flow from there further into the auxiliary collecting chamber 20, 30, 40 via the auxiliary duct section 21, 38, 39.

Figure 3:
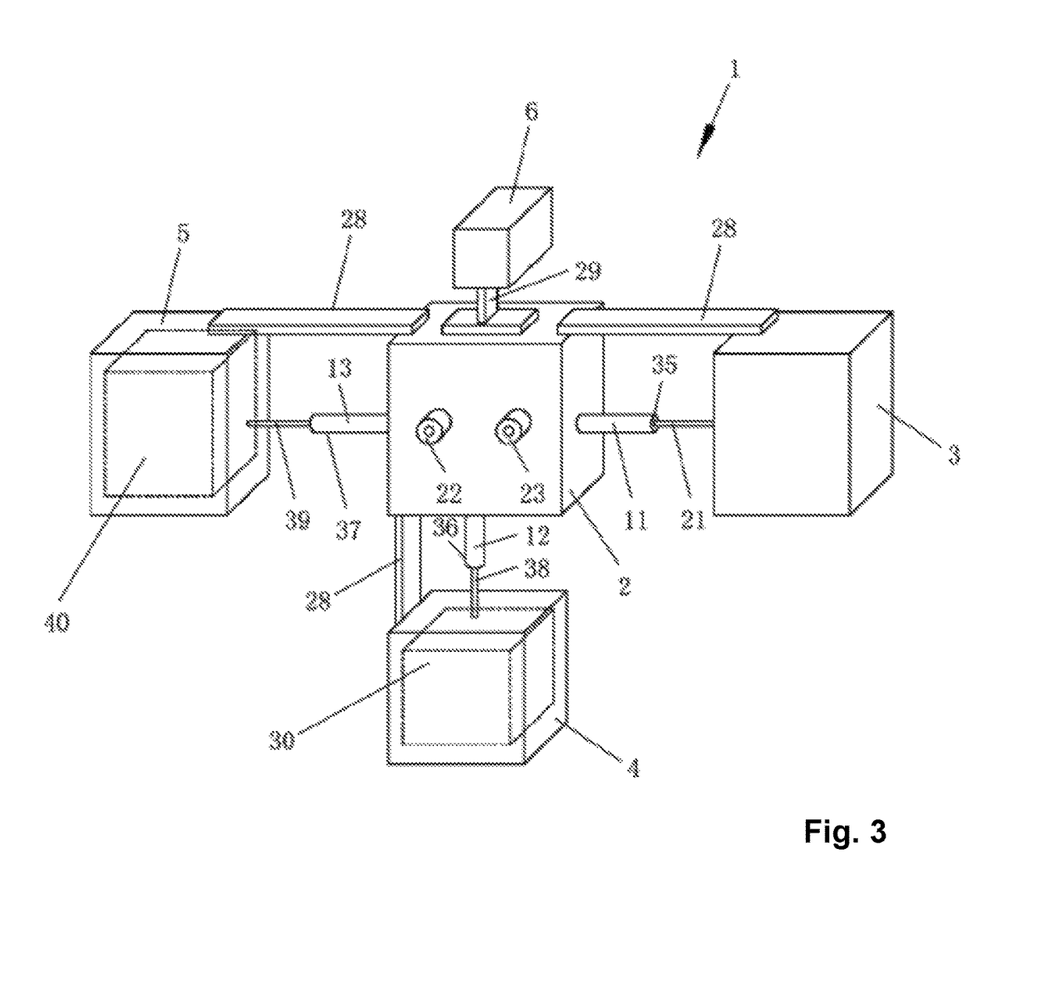
FIG. 3 is a schematic view of the system with three auxiliary collecting chambers and a holder.

FIG. 3 shows a system 1 with the main container 2 and with the first auxiliary container 3 according to FIG. 2a. Another auxiliary container 4 has a second auxiliary collecting chamber 30, which is connected to the second main duct section 12 via a second auxiliary duct section 38. The second auxiliary duct section 38 and the second main duct section 12 now form a second duct 36. A third auxiliary container 5 has a third auxiliary collecting chamber 40, which is connected to the third main duct section 13 via a third auxiliary duct section 39. The third auxiliary duct section 39 and the third main duct section 13 now form a third duct 37. The explanations given above for the first auxiliary duct section 21 and the first duct 35 correspondingly apply to the configuration of the second and third auxiliary duct sections 38, 39 and of the second and third ducts 36, 37. In particular, as was described above in connection with the first auxiliary duct section 21, respective water-soluble closing components may be arranged in the second and third auxiliary duct sections 38, 39. The configuration and the connection of the second and third auxiliary containers 4, 5 thus correspond to those of the first auxiliary container 3.

The main container 2 is fastened to a carrying component 6 via a connection component 29. The carrying component 6 may be a standard rail and is used to fasten the system 1, for example, on a ceiling-mounted supply unit, on a wall or on an operating table. Other possibilities of fastening are not, of course, ruled out.

The arrangement shown in FIG. 3 may, of course, also be formed with a main container 2 according to FIG. 2b.

A gel 27, which absorbs the liquid flowing through the liquid inlet 23 may be arranged in the main collecting chamber 10 and the auxiliary collecting chambers 20, 30, 40. The gel 27 now swells with increasing uptake of liquid and fills in this manner the respective collecting chamber 10, 20, 30, 40. Since the gel 27 has a higher viscosity than the absorbed liquid, liquid is prevented by the gel 27 from sloshing around.

If the liquid level in the main collecting chamber 10 rises to the extent that the volume is not sufficient to absorb all the liquid even on adding all auxiliary collecting chambers 20, 30, 40. a hydrophobic diaphragm component 25, which is permeable to gas but is a barrier for liquid, is arranged at the suction pump port 22. As soon as the liquid reaches the hydrophobic diaphragm component 25, no more liquid can be absorbed into the system 1, because the liquid blocks the flow of gas through the hydrophobic diaphragm component 25.

For protection against bacteria and viruses, a filter element 24, which is configured as a bacteria and virus filter, is provided at the suction pump port 22. Bacteria and viruses, which, removed by the liquid, are drawn by the vacuum of the pump into the suction pump port 22, are filtered out in the bacteria and virus filter 24. Contamination of the suction pump port 22 and of the downstream pump stages with bacteria or viruses is thus avoided.

The system 1 may be manufactured, for example, from polypropylene (PP) or polyethylene (PE). These are hygienic materials, which are lightweight and sufficiently stable in case of wall thicknesses of 1 mm to 2 mm at a suction pressure of 950 mbar.

The auxiliary containers 3, 4, 5 may have identical design. This simplifies the manufacture and the operation of the system 1.

The main collecting chamber 10 may have a collection volume of, e.g., 700 mL to 1,000 mL. The evacuation times are still short and the weight of a full main container 2 is still manageable in this range of collection volumes.

The auxiliary collecting chambers 20, 30, 40 may have a volume of 550 mL to 800 mL.

While specific embodiments of the invention have been shown and described in detail to illustrate the application of the principles of the invention, it will be understood that the invention may be embodied otherwise without departing from such principles.

What is claimed is:

1. A system for collecting liquid, the system comprising:
a main container defining a main collecting chamber;
a suction pump port connected to said main container and in fluid communication with said main collecting chamber for establishing a vacuum in said main collecting chamber;
a liquid inlet opening connected to said main container and in fluid communication with said main collecting chamber for drawing liquid into the main collecting chamber through said liquid inlet opening based on the vacuum in said main collecting chamber;
a main duct section connected to said main container, wherein said main duct section is in fluid communication with said main collecting chamber at a location along a liquid fill path of said main collecting chamber;
an auxiliary container defining an auxiliary collecting chamber;
an auxiliary duct section connected to said auxiliary collecting chamber in a fluid-communicating manner for connection to said main duct section, wherein said main duct section and said auxiliary duct section form a duct when said main duct section is connected to said auxiliary duct section; and
a water-soluble closing component operatively connected to said duct and closing said duct such that said main collecting chamber is separated by said water-soluble closing component from said auxiliary collecting chamber, whereby upon liquid filling said main collecting chamber to said location along the liquid fill path, said water-soluble closing component comes into contact with liquid and dissolves and opens said duct.

2. A system in accordance with claim 1, wherein said water-soluble closing component is arranged in said main duct section.

3. A system in accordance with claim 1, wherein said water-soluble closing component is arranged at said auxiliary duct section, and said auxiliary collecting chamber is pre-evacuated to define an auxiliary collecting chamber vacuum therein, whereby upon said water-soluble closing component coming into contact with liquid, said water-soluble closing component dissolves such that said auxiliary duct section is not separated from the auxiliary collecting chamber and the duct is exposed to the auxiliary collecting chamber vacuum in the auxiliary collecting chamber.

4. A system in accordance with claim 1, wherein said main duct section has a blocking component, said blocking component closing said main duct section when said main duct section and said auxiliary duct section are separated from one another, and said blocking component opening said main duct section when said main duct section is connected to said auxiliary duct section.

5. A system in accordance with claim 1, further comprising a gel arranged in said main collecting chamber and in said auxiliary collecting chamber.

6. A system in accordance with claim 1, further comprising:
another auxiliary collecting chamber to provide at least two auxiliary collecting chambers;
another auxiliary duct section to provide at least two auxiliary duct sections, said main collecting chamber being in fluid communication with at least two main duct sections, each of said at least two auxiliary duct sections being connected to one of said at least two auxiliary collecting chambers in a fluid-communicating manner for connection to one of said at least two main duct sections, each of said main duct sections and one of said auxiliary duct sections forming a respective duct when said main duct sections and said auxiliary duct sections are connected to one another, wherein a respective water-soluble closing component closes said respective duct.

7. A system in accordance with claim 6, wherein each of said main duct sections comprises an overflow edge component, said overflow edge component of each of said main duct sections being arranged between said main collecting chamber and a respective main duct section, said overflow edge component of each of said main duct sections having a different distance from a bottom component of said main collecting chamber.

8. A system in accordance with claim 1, further comprising an overflow edge component arranged at said location along the liquid fill path and allowing liquid from said main collecting chamber into said main duct section only upon reaching an overflow edge of said overflow edge component.

9. A system in accordance with claim 8, wherein said water-soluble closing component is arranged in said main duct section horizontally, whereby liquid that flows over the overflow edge will collect on said water-soluble closing component prior to dissolving.

10. A device for collecting liquid, the device comprising:
a main container defining a main collecting chamber;
a suction pump port connected to said main container and in fluid communication with said main collecting chamber for establishing a vacuum in said main collecting chamber;
a liquid inlet opening connected to said main container and in fluid communication with said main collecting chamber for drawing liquid into the main collecting chamber through said liquid inlet opening based on the vacuum in said main collecting chamber;
a main duct section connected to said main container, wherein said main duct section is in fluid communication with said main collecting chamber at a location along a liquid fill path of said main collecting chamber;
a water-soluble closing component operatively connected to said main duct section and closing said main duct section such that one portion of main duct section is separated by said water-soluble closing component from the main collecting chamber until said water-soluble closing component is dissolved by contact with liquid, whereby upon liquid filling said main collecting chamber to said location along the liquid fill path, said water-soluble closing component comes into contact with liquid and dissolves such that said one portion of main duct section is not separated from the main collecting chamber.

11. A device in accordance with claim 10, further comprising a blocking component operatively connected to said main duct section, said blocking component closing said main duct section when said main duct section is separated from an auxiliary duct section, said main duct section being configured to connect to said auxiliary duct section, said blocking component opening said main duct section when said main duct section is connected to said auxiliary duct section providing fluid communication between said auxiliary duct section and said one portion of main duct section.

12. A device in accordance with claim 10, further comprising a gel arranged in said main collecting chamber.

13. A device in accordance with claim 10, wherein said main collecting chamber is in fluid communication with at least two main duct sections, each of said at least two main duct sections being configured to connect to an auxiliary duct section to form a respective duct for connecting said main collecting chamber to an auxiliary collecting chamber in a fluid-communicating manner, wherein a respective water-soluble closing component closes said respective duct.

14. A device in accordance with claim 13, wherein each of said main duct sections comprises an overflow edge component, said overflow edge component of each of said main duct sections being arranged between said main collecting chamber and a respective main duct section, said overflow edge component of each of said main duct sections having a different distance from a bottom component of said main collecting chamber.

15. A device in accordance with claim 10, further comprising an overflow edge component arranged at said location along the liquid fill path and allowing liquid from said main collecting chamber into said main duct section only upon reaching an overflow edge of said overflow edge component.

16. A system in accordance with claim 15, wherein said water-soluble closing component is arranged in said main duct section horizontally, whereby liquid that flows over the overflow edge will collect on said water-soluble closing component prior to dissolving.

17. A device for collecting liquids, the device comprising:
an auxiliary container defining an auxiliary collecting chamber, said auxiliary collecting chamber being pre-evacuated to define a vacuum therein;
an auxiliary duct section connected to said auxiliary collecting chamber, wherein said auxiliary duct section is in fluid communication with said auxiliary collecting chamber;
a water-soluble closing component operatively connected to said auxiliary duct section and closing said auxiliary duct section such that an inlet of said auxiliary duct section is separated by said water-soluble closing component from the auxiliary collecting chamber until said water-soluble closing component is dissolved by contact with liquid, whereby upon the inlet of said auxiliary duct section being exposed to liquid, said water-soluble closing component comes into contact with liquid and dissolves such that said the inlet of said auxiliary duct section is not separated from the auxiliary collecting chamber and is exposed to the vacuum in the auxiliary collecting chamber.

18. A device in accordance with claim 17, further comprising a gel arranged in said auxiliary collecting chamber.

19. A device in accordance with claim 17, further comprising:
another auxiliary collecting chamber to provided at least two auxiliary collecting chambers;
another auxiliary duct section to provide at least two auxiliary duct sections, each of said at least two auxiliary ducts being configured to connect to a main duct section to form a respective duct for connecting one of said auxiliary connecting chambers to a main collecting chamber in a fluid-communicating manner, wherein a respective water-soluble closing component closes said respective duct.

* * * * *